United States Patent
Girod et al.

(10) Patent No.: US 11,207,113 B2
(45) Date of Patent: Dec. 28, 2021

(54) OSTEOSYNTHESIS SCREW COMPRISING AN ANGULAR INDEX IN RELATION TO THE SCREWDRIVER

(71) Applicant: NOVASTEP, Saint-Gregoire (FR)

(72) Inventors: Loïc Girod, Goven (FR); Rémi Le Besque, Bruz (FR)

(73) Assignee: NOVASTEP, Saint-Gregoire (FR)

( * ) Notice: Subject to any disclaimer, the term of this patent is extended or adjusted under 35 U.S.C. 154(b) by 264 days.

(21) Appl. No.: 16/483,230

(22) PCT Filed: Feb. 20, 2018

(86) PCT No.: PCT/FR2018/050396
§ 371 (c)(1),
(2) Date: Aug. 2, 2019

(87) PCT Pub. No.: WO2018/154225
PCT Pub. Date: Aug. 30, 2018

(65) Prior Publication Data
US 2020/0229853 A1 Jul. 23, 2020

(30) Foreign Application Priority Data
Feb. 22, 2017 (FR) ...................................... 1751390

(51) Int. Cl.
*A61B 17/86* (2006.01)
*A61B 17/88* (2006.01)

(52) U.S. Cl.
CPC ........ *A61B 17/8615* (2013.01); *A61B 17/888* (2013.01)

(58) Field of Classification Search
CPC ............ A61B 17/8615; A61B 17/8645; A61B 17/888
See application file for complete search history.

(56) References Cited

U.S. PATENT DOCUMENTS

| | | | |
|---|---|---|---|
| 6,953,463 B2* | 10/2005 | West, Jr. ............... | A61F 2/0811 |
| | | | 606/326 |
| 2001/0041937 A1 | 11/2001 | Rieser et al. | |
| 2009/0163961 A1 | 6/2009 | Kirschman | |
| 2014/0081339 A1* | 3/2014 | Bowman ............ | A61B 17/8888 |
| | | | 606/304 |

FOREIGN PATENT DOCUMENTS

| | | |
|---|---|---|
| WO | 2015/077327 A1 | 5/2015 |
| WO | 2015/185828 A1 | 12/2015 |

OTHER PUBLICATIONS

May 22, 2018 International Search Report issued in International Patent Application No. PCT/FR2018/050396.

* cited by examiner

*Primary Examiner* — Olivia C Chang
(74) *Attorney, Agent, or Firm* — Oliff PLC

(57) ABSTRACT

A tightening screw for osteosynthesis, including a screw thread that is arranged along a main axis, and including, at its distal end, a recess that has regular shapes about the main axis which are distributed angularly and are suitable for receiving complementary shapes of a screwdriver engaging therewith; the rear face of the screw is inclined in relation to a transverse plane of the screw, the screw being characterized in that the recess in the screw includes at least one specific shape that is different from the other, regular shapes.

9 Claims, 3 Drawing Sheets

Fig. 1a
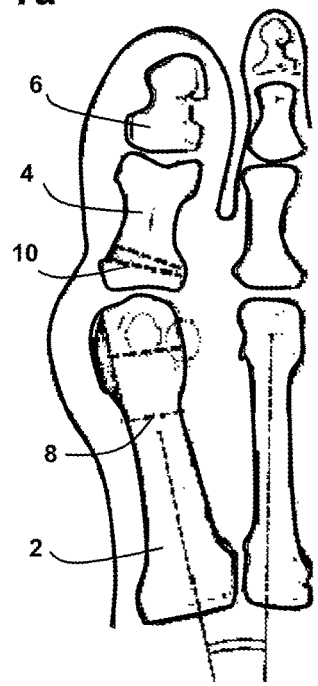
Fig. 1b
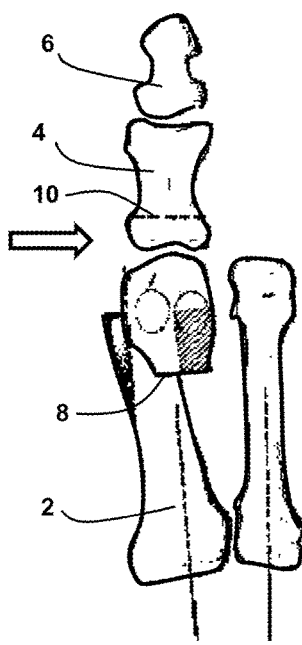
Fig. 1c
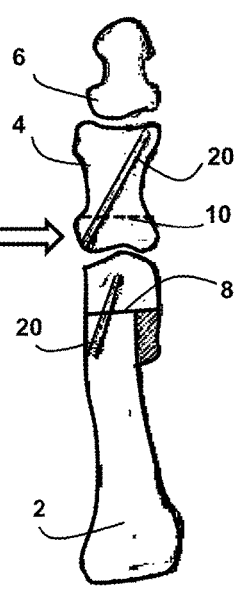
Fig. 2
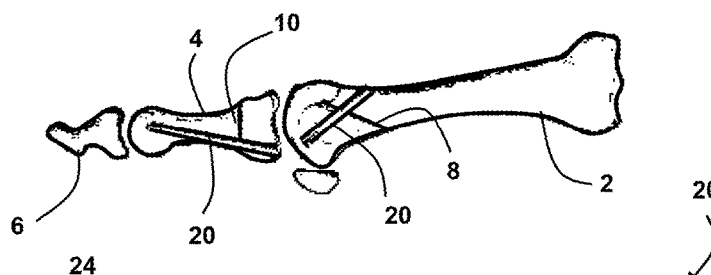
Fig. 3
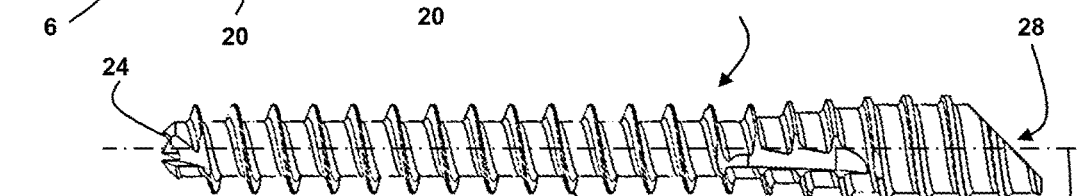
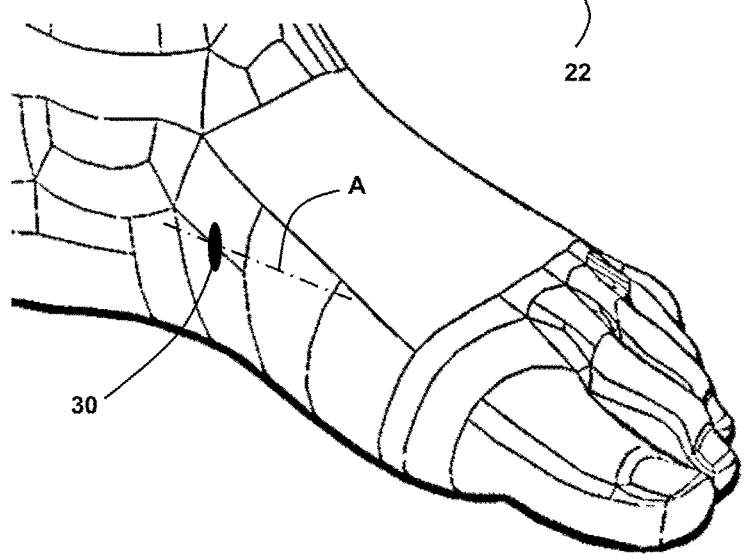
Fig. 4

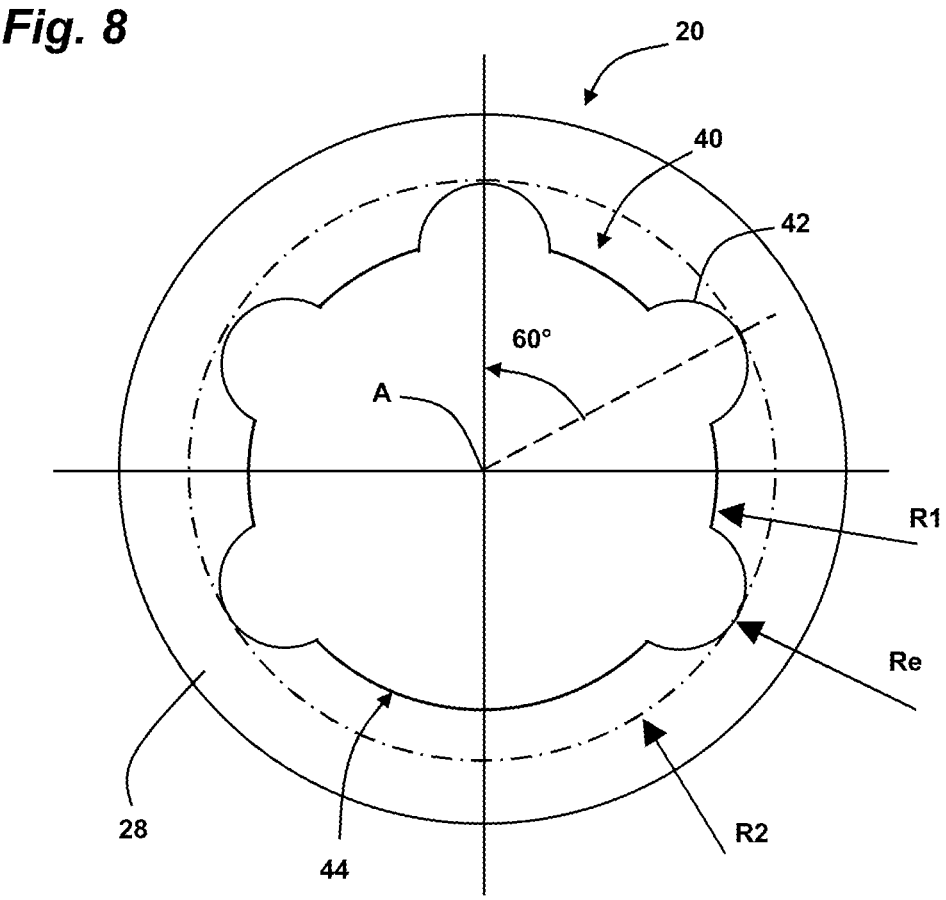

OSTEOSYNTHESIS SCREW COMPRISING AN ANGULAR INDEX IN RELATION TO THE SCREWDRIVER

The present invention concerns a tightening screw provided to be actuated by a screwdriver, and a screwdriver adapted for this tightening screw. In particular the invention can be applied to the field of bone repair surgery, in particular for tightening and fixing an osteosynthesis screw in a bone fragment to be stabilized. More particularly, the invention can be applied to the limb ends surgery, such as feet, ankles, hands or wrists.

The osteosynthesis is a surgery that consists in fixing therebetween two bone portions such as fragments of a cut or broken bone, or two bones close to each other, thanks to axial elements such as screws or wires made of metal materials tolerated by the body, having a shape adapted to the elements to be treated.

In particular, the osteosynthesis can be applied for chevron-type osteotomy surgeries, in a minimally invasive approach.

The hallux-valgus is a frequent deformation of the forefoot which results in an inward deviation called varus of the first metatarsus, and an outward deviation called valgus of the first phalanx. One type of surgical procedure allowing correcting this deformation includes a chevron osteotomy, which is then fixed by one or several osteosynthesis screw(s) in a minimally invasive approach.

The minimally invasive surgical approach consists in performing small incisions in the skin and tissues for passing the instruments and implants necessary for correction. The size of the scars is thus minimized, which offers a faster rehabilitation of the tissues compared to a conventional open-air approach.

The screws used for the osteosynthesis include a totally or partially tapped length, and a rear head comprising at the tip thereof a hollow imprint provided to be actuated by a screwdriver. In particular, the heads may have a beveled rear end face, generally inclined at 45° with respect to the main axis of the screw, which should be disposed in a particular orientation in order to conform to the outer contour of the bone after the complete introduction of this screw thereinside, to limit the damage of the surrounding tissues.

For a minimally invasive surgery with this type of screw, as the final tightening phase of the screw in the bone site approaches, the tissues may visually hide the beveled rear face of the screw.

Moreover, a type of hollow imprint known for an osteosynthesis screw, disclosed in particular by the document WO-A1-2015185828, includes six lobes distributed circumferentially around the axis, receiving a complementary male shape formed at the tip of the screwdriver.

The generally cylindrical shape with six lobes of the screw or the screwdriver further has on some lobes a slightly conical portion enabling by axial thrust a small tightening of the screwdriver in the imprint, in order to ensure a temporary holding of the screw at the tip of the screwdriver. In this way, it is possible to avoid a loss of connection of the screwdriver with the screw before or during mounting.

In addition, for a screw having a beveled rear face, it is known to use a screwdriver having a visual marker indicating an orientation about its axis, which allows by fixing the screw on the screwdriver in a particular way with respect to this marker, knowing at all times at the end of screwing the position of this inclined rear face when it is no longer visible.

Nonetheless, if the screwing is not completed while the rear face of the screw hidden by the tissue is no longer apparent, in case of uncoupling of the screwdriver off the imprint of the screw, for example during a wrong maneuver, the surgeon must carry out a complementary surgery to find the inclination of this rear face, such as unscrewing of the screw, or taking of an X-ray image visualizing this inclination. There is then a loss of time during the surgery of the patient which is harmful.

The present invention aims in particular at avoiding these drawbacks of the prior art.

It proposes for this purpose a tightening screw for osteosynthesis including a tapping disposed along a main axis, and its rear end an imprint having around the main axis angularly distributed regular shapes, adapted to receive complementary shapes of a screwdriver, the rear face of the screw having an inclination with respect to a transverse plane of the screw, this screw being remarkable in that its imprint includes at least one particular shape different from the other regular shapes.

An advantage of this tightening screw is that by making on the front end of the screwdriver shapes complementary with those of the screw, comprising a complementary particular shape, a unique orientation of the screwdriver fitted on the imprint of the screw is obtained.

In case of uncoupling of the screwdriver before the end of the tightening operation while the rear face of the screw is no longer visible, the surgeon gently rotates the screwdriver by exerting a slight pressure until its engagement on the imprint of this screw, thus allowing finding the unique orientation imposed by the particular shape.

The surgeon then completes his tightening by monitoring a visual orientation marker of the screwdriver, to determine with certainty the orientation of the inclined rear face of the screw.

The tightening screw for osteosynthesis according to the invention may furthermore include one or more of the following features, which may be combined together.

Advantageously, the tightening screw includes five regular shapes. Thus, this is close to screw imprints that generally have six regular shapes.

Advantageously, the particular shape covers about the axis an angular sector equivalent to that of a regular shape. This type of imprint can be easily derived from a known imprint including six regular shapes.

According to one embodiment, the regular shapes constitute lobes disposed on a crown centered on the axis, comprised between an internal circle with a small radius and an external circle with a large radius. This type of shape allows transmitting a high torque.

According to another embodiment, the regular shapes include a first circular arc centered on the axis, then a second circular arc projecting outwardly with respect to this first circular arc.

Advantageously, the particular shape has a constant radius which is centered on the axis.

In this case, the constant radius of the particular shape may be the small radius of the internal circle of the regular shapes constituting lobes.

Advantageously, the imprint includes a generally cylindrical shape disposed parallel to the axis, comprising a slightly conical portion. This conical portion enables a blocking on the screwdriver.

According to one embodiment, the tapping of the screw extends over the entire length of this screw, and has a larger diameter at the rear side of the screw.

According to another embodiment, the screw includes a front tapping extending over a front portion of the length of the screw, and a head tapping disposed at the rear of this screw, separated from the front tapping, having a larger diameter than this front tapping.

The invention also relates to a screwdriver provided to tighten screws having any one of the preceding features, including at the front a tip having shapes complementary with those of the imprint of the screws enabling fitting thereupon.

Advantageously, the screwdriver includes a visual angular marker.

Advantageously, the tip of the screwdriver includes a generally cylindrical shape disposed parallel to the axis, comprising a slightly conical portion. This conical portion enables a blocking of the screw on the screwdriver.

Other features and advantages of the invention will appear on reading the following description, provided only as example, with reference to the following appended figures:

FIGS. 1a, 1b and 1c have successively on a foot in top view, three steps of a surgery for reducing a hallux valgus of the big toe;

FIG. 2 is a side view of this foot after the procedure;

FIG. 3 shows a screw according to the invention used for this procedure;

FIG. 4 is an external view of the foot after the insertion of the screw;

FIG. 8 shows a screw according to one variant.

For more clarity, identical or similar elements are marked with identical reference signs on all the figures.

Figure 5:
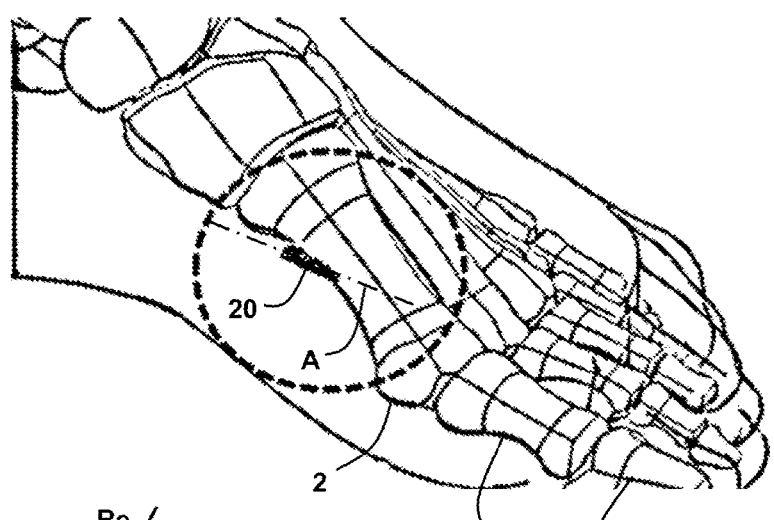
FIG. 5 is an overview of the bones of the foot showing the insertion of the screw on the metatarsus.

FIG. 1a shows a foot including successively forwards of the big toe, a metatarsus 2, a proximal phalanx 4 and a distal phalanx 6.

The internal side of the foot is that facing the axis of the body. The metatarsus 2 has an abnormal inward inclination, and the proximal phalanx 4 has an abnormal outward inclination.

The first step of the surgery provides for a cut 8 of the metatarsus 2 at the front portion thereof, formed at a slant, and a double cut 10 of the proximal phalanx 4 at the rear portion thereof in order to remove a portion of the bone forming a corner.

FIG. 1b shows the displacement of the front portion of the metatarsus 2 outwardly relative to the rear portion, and a recovery of the proximal phalanx 4 inwardly by having removed the portion of the bone forming the corner. A substantially alignment along the axis of the foot, the metatarsus 2 and the proximal phalanx 4 thus modified is obtained.

FIG. 1c and FIG. 2 show the insertion of a first tightening screw 20 into the two portions of the metatarsus 2 and of a second screw into the two portions of the proximal phalanx 4, each time to fix together these two portions.

Each tightening screw 20 comes into the internal side of the foot from the rear, after having made a minimum incision on the tissues disposed in the axis A of the screw.

FIG. 3 shows a screw 20 including a tapping 22 over its entire length, comprising a diameter which increases gradually at a rear portion. The front end of the screw 20 ends in a shape 24 ensuring the formation of the tapping in the bone portions.

The planar rear end face 28 of the screw 20 has an inclination with respect to a transverse plane of the screw, forming a bevel which may be of 45°. This end face 28 includes an axially directed hollow imprint, centered on the axis of the screw A, provided to receive a shape complementary with a screwdriver in order to drive it in rotation.

Alternatively, the screw may be a compression screw including a front tapping extending over a front portion of its length, then a smooth portion, and finally a head tapping disposed at the rear of this screw, having a larger diameter than the front tapping.

FIGS. 4 and 5 have a small incision 30 formed on the internal side of the foot, enabling fitting of the tools to cut the tissues and insert a screw 20 on the metatarsus 2. Other incisions enable cutting of the bones 2, 4, and the insertion of the second screw 20. In this way, a minimum of trauma on the tissues is achieved.

At the end of tightening of the screws 20, the angular position of each screw is adjusted so as to substantially align its beveled rear face 28 on the external surface of the bone, in order to ensure minimum stress or trauma to the surrounding tissues.

Figure 6:
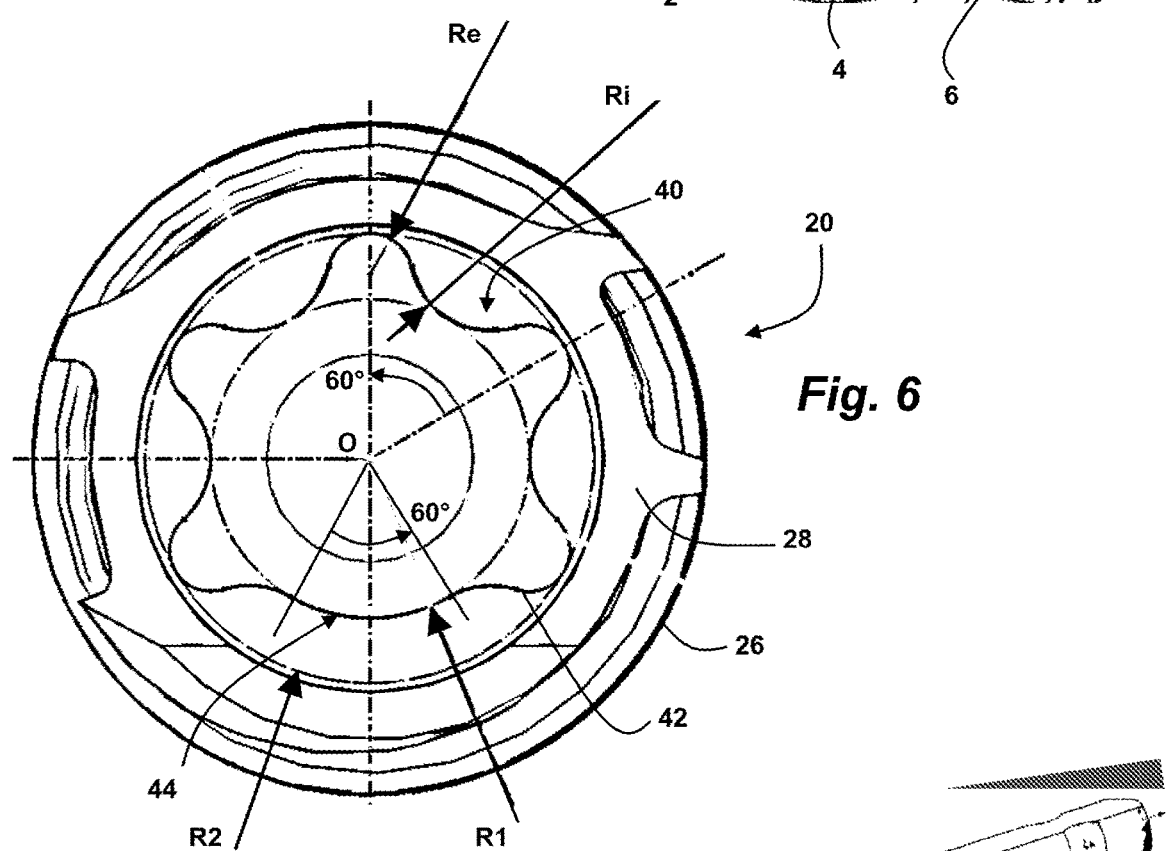
FIG. 6 is a rear view of the screw showing its drive imprint.

FIG. 6 shows the hollow imprint 40 formed on the rear face 28 of the screw 20, constituting a cylinder parallel to the axis of the screw A, comprising a succession of five identical shapes which consist of regular lobes 42 disposed on a crown centered on the axis, comprised between an internal circle with a small radius R1 and an external circle with a large radius R2.

Each of the five lobes 42 of the recess of the imprint 40 disposed at an angle of 60° with respect to the center O, successively includes a concave radius Re then a convex radius Ri. An angle of 60° includes a particular circular arc shape 44, devoid of any lobe, which follows the internal circle with a small radius R1.

The star-shaped imprint 40 may in particular replicate an imprint known under the trade name <<Torx>>, with one lobe less.

Figure 7:
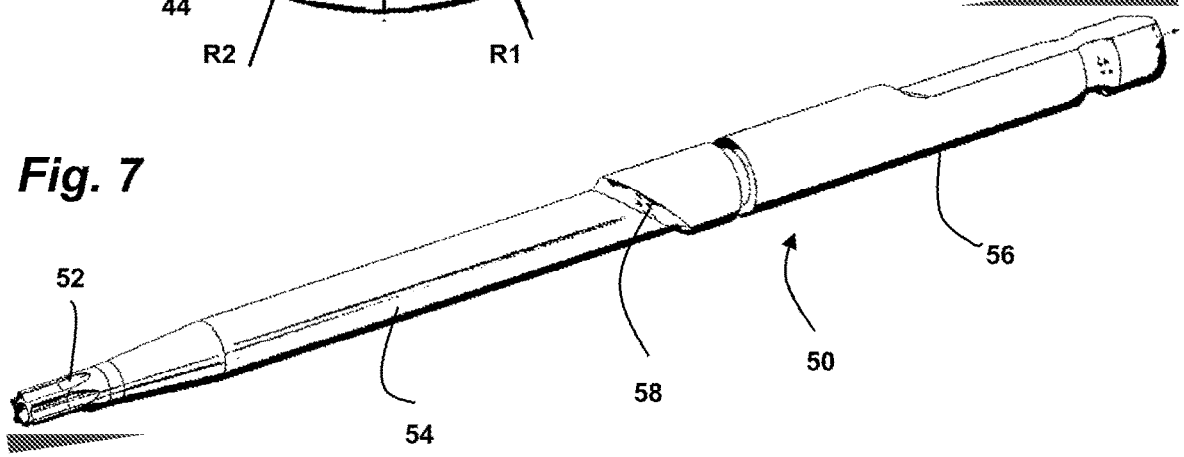
FIG. 7 shows a screwdriver provided for this screw.

FIG. 7 shows a screwdriver 50 including, at the front of a metal cylindrical rod 54, a tip 52 constituting a cylinder centered on the axis, provided to fit with a minimum clearance in the imprint 40 of the rear face 28 of the screw 20.

In particular, the front tip 52 includes a succession of five shapes constituting regular lobes, each extending at an angle of 60°. Over the remaining 60°, we have a circular portion devoid of any lobe, which follows the internal circle with a radius R1.

A unique positioning of the screw 20 on the screwdriver 50 is obtained, which is provided by the adjustment of the two circular portions on one another. For the initial mounting of the screw 20 on the screwdriver 50, or after beginning the insertion if the surgeon disengages the screwdriver off the screw and then want to put it back, the unique angular positioning is necessarily obtained.

In particular, the imprint 40 of the screw 20 or the front tip 52 of the screwdriver 50 may include on some lobes a slightly conical shape opening at the rear of the screw or closing at the front of the screwdriver, in order to ensure after an axial thrust, a holding of the screw on the screwdriver, as disclosed in the document of the prior art mentioned hereinabove.

The screwdriver 50 includes at the rear a connection area for a handle 56, having a front face 58 forming a bevel inclined at 45°, disposed parallel to the beveled rear face 28 of the screw 20 when it is fixed on the screwdriver. In this way, the surgeon visualizes directly by looking at the handle the angular position of the beveled rear face 28 of the screw 20.

FIG. 8 alternatively has an imprint 40 formed on the rear face 28 of the screw 20, constituting a cylinder parallel to the axis of the screw A, comprising a succession of five identical regular shapes each covering an angle of 60°, comprised between the circles centered on the axis A, with the small radius R1 and the large radius R2.

Each regular shape includes a circular arc that follows the small radius R1, then a lobe 42 formed by a circular arc with a convex radius Re turned, which extends up to the external circle with a large radius R2.

One of the lobes is absent leaving instead over a 60° angle a particular shape in form of a circular arc 44 which follows the internal circle with a small radius R1.

A method for manufacturing the imprint 40 of the screw 20, simple to implement, includes a succession of five drillings to form the lobes 42, then a milling centered on the axis along the small radius R1, to complete the cylindrical shape of this imprint.

The screw 20 according to the invention as well as the specific screwdriver 50 ensure to the surgeon easiness, safety and speed in the execution of surgeries using this type of screw.

Alternatively, the imprint 40 of the screw 20 may have other shapes. In particular, standardized shapes can be used, such as a hexagonal shape which is easier to make but has a reduced torque transmitting capacity.

The invention claimed is:

1. A tightening screw for osteosynthesis comprising:
a thread disposed along a main axis;
a rear end having an inclination with respect to a transverse plane of the screw; and
a hollow in the rear end, the hollow having:
   a plurality of radially distributed identical lobes disposed on a crown centered on the main axis and disposed between an internal circle with a smaller radius and an external circle with a larger radius; and
   at least one particular shape which has a design different from a design of the plurality of lobes, the plurality of lobes and the at least one particular shape being adapted to receive complementary shapes of a screwdriver fitting thereupon.

2. The tightening screw according to claim 1, wherein the plurality of lobes includes five lobes.

3. The tightening screw according to claim 1, wherein the particular shape covers an angular sector about the axis equivalent to that of one of the plurality of lobes.

4. The tightening screw according to claim 1, wherein the plurality of lobes include a first circular arc centered on the axis, then a second circular arc projecting outwardly with respect to the first circular arc.

5. The tightening screw according to claim 1, wherein the particular shape has a constant radius which is centered on the axis.

6. The tightening screw according to claim 1, wherein the hollow includes a generally cylindrical shape disposed parallel to the axis, comprising a slightly conical portion.

7. The tightening screw according to claim 1, wherein its thread extends over an entire length of the screw, and has a larger diameter at a rear side of this screw.

8. The tightening screw according to claim 1, wherein it includes a front thread extending over a front portion of a length of the screw, and a head thread disposed at a rear of the screw, separated from the front thread, having a larger diameter than the front thread.

9. A screwdriver provided to tighten screws according to claim 1 including at a front a tip having shapes complementary with those of the hollow enabling fitting thereupon, including a visual angular marker, wherein the tip includes a generally cylindrical shape disposed parallel to the axis, comprising a slightly conical portion.

* * * * *